US012728289B2

(12) United States Patent
Kang et al.

(10) Patent No.: US 12,728,289 B2
(45) Date of Patent: Sep. 8, 2026

(54) METHOD AND APPARATUS FOR CARRYING OUT DOSE DELIVERY QUALITY ASSURANCE FOR HIGH-PRECISION RADIATION TREATMENT

(71) Applicants: THE CATHOLIC UNIVERSITY OF KOREA INDUSTRY-ACADEMIC COOPERATION FOUNDATION, Seoul (KR); AJOU UNIVERSITY INDUSTRY-ACADEMIC COOPERATION FOUNDATION, Suwon-si (KR)

(72) Inventors: Young Nam Kang, Seoul (KR); Ji Na Kim, Suwon-si (KR); Hong Seok Jang, Seoul (KR); Byung Ock Choi, Seoul (KR); Yun Ji Seol, Guri-si (KR); Tae Geon Oh, Namyangju-si (KR); Na Young An, Seoul (KR); Jae Hyeon Lee, Seoul (KR); Kyu Min Han, Chungcheongbuk-do (KR); Ye Rim Shin, Seoul (KR)

(73) Assignees: THE CATHOLIC UNIVERSITY OF KOREA INDUSTRY-ACADEMIC COOPERATION FOUNDATION, Seoul (KR); AJOU UNIVERSITY INDUSTRY-ACADEMIC COOPERATION FOUNDATION, Suwon-si (KR)

( * ) Notice: Subject to any disclaimer, the term of this patent is extended or adjusted under 35 U.S.C. 154(b) by 628 days.

(21) Appl. No.: 18/268,489

(22) PCT Filed: Dec. 22, 2021

(86) PCT No.: PCT/KR2021/019634
§ 371 (c)(1),
(2) Date: Jun. 20, 2023

(87) PCT Pub. No.: WO2022/139471
PCT Pub. Date: Jun. 30, 2022

(65) Prior Publication Data

US 2024/0075318 A1 Mar. 7, 2024

(30) Foreign Application Priority Data

Dec. 24, 2020 (KR) ........................ 10-2020-0183301
Dec. 14, 2021 (KR) ........................ 10-2021-0178200

(51) Int. Cl.
*G16H 40/20* (2018.01)
*A61N 5/10* (2006.01)

(52) U.S. Cl.
CPC ......... *A61N 5/1075* (2013.01); *A61N 5/1045* (2013.01); *G16H 40/20* (2018.01)

(58) Field of Classification Search
CPC .. A61N 5/1075; A61N 5/1045; A61N 5/1031; A61N 5/103; A61N 5/10;
(Continued)

(56) References Cited

U.S. PATENT DOCUMENTS

2007/0041499 A1* 2/2007 Lu ........................ A61N 5/1048 378/65
2017/0203129 A1* 7/2017 Dessy .................. A61N 5/1071
(Continued)

FOREIGN PATENT DOCUMENTS

KR 10-1435497 B1 8/2014
KR 10-1734938 B1 5/2017
(Continued)

OTHER PUBLICATIONS

Kim, J. et al. "Analysis of the effect of tomotherapy plan parameters on patient-specific delivery quality assurance (DQA)". Journal of the Korean Physical Society. Dec. 2019, vol. 75, No. 12, pp. 1043-1047.

(Continued)

*Primary Examiner* — Brian L Casler
(74) *Attorney, Agent, or Firm* — Bridgeway IP Law Group, PLLC; Sang Ho Lee; Hyun Woo Shin

(57) ABSTRACT

The present disclosure relates to a method for carrying out dose delivery quality assurance for high-precision radiation treatment, in which parameters affecting a pass rate of dose delivery quality assurance can be derived through regression analysis, which is a known statistical analysis method, and a pass rate prediction model capable of predicting each parameter and the pass rate of dose delivery quality assurance can be derived, and accordingly, it can be predicted in advance whether dose delivery quality assurance will be passed according to the parameters through the above prediction model, without repeatedly carrying out dose delivery quality assurance according to a patient's treatment plan, and as a result, the efficiency of dose delivery quality assurance can be enhanced, and the time or capacity required for such quality assurance is reduced, such that radiation treatment for an actual patient can be quickly and precisely carried out.

4 Claims, 12 Drawing Sheets

(58) Field of Classification Search
CPC ...... A61N 5/1038; G16H 40/20; G16H 20/40; G16H 10/60; G16H 50/70; G16H 50/30; G16H 50/50; A61B 34/10
USPC ........................................................ 600/1
See application file for complete search history.

(56) References Cited

U.S. PATENT DOCUMENTS

2018/0085168 A1* 3/2018 Valdes ............ G06Q 10/06395
2020/0197726 A1* 6/2020 Cordero Marcos .. A61N 5/1031

FOREIGN PATENT DOCUMENTS

KR 10-1882300 B1 7/2018
KR 10-1937651 B1 1/2019
KR 10-1996268 B1 7/2019
WO WO-2007014108 A2 * 2/2007 ............ A61N 5/103

OTHER PUBLICATIONS

Kyung Hwan Chang et al., "Statistical analysis of treatment planning parameters for prediction of delivery quality assurance failure for helical tomotherapy". Technology in Cancer Research & Treatment, 2020, vol. 19, pp. 1-9. published online Dec. 11, 2020.

* cited by examiner

Statistical analysis (Regression analysis)

*Tool : IBM SPSS 25*

$R^2$ (Percent of variance explained)

$$R^2 = 1 - \frac{\text{MSE of regression line}}{\text{MSE of the average of the data}}$$

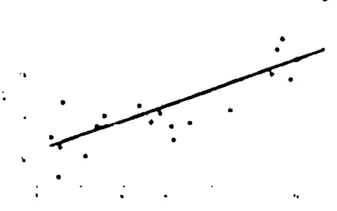

Durbin Watson (DW)

1 < DW < 3 ; no autocorrelation

Autocorrelation = the errors of adjacent observations are correlated.

Analysis of variance (ANOVA)

$p < 0.05$, the regression equation is appropriate.

Variance Inflation Factors (VIF)

VIF <10, no problem with multicollinearity.

Multicollinearity ; similar variables are included in independent variables.

Beta (β)

closer to 1, the stronger the influence the influence of the independent variable on the dependent variable.

t the coefficient divided by the standard error.

The degree of standard deviation can be determined relatively.

FIG. 6

Regression analysis of Tomo_H
(Model summary)

*[Model Summary]*

| | R | R Square | Adjusted R Square | Std. Error of the Estimate | Durbin-Watson |
|---|---|---|---|---|---|
| **Model** | 0.496 | 0.246 | 0.201 | 1.56985 | 1.774 |

*[ANOVA]*

| | Sum of square s | df | Mean Square | F | Sig. |
|---|---|---|---|---|---|
| **Regression** | 109.139 | 8 | 13.642 | 5.536 | 0.000 |
| **Residual** | 335.163 | 136 | 2.664 | | |
| **Total** | 444.301 | 144 | | | |

**df : Degree of freedom*

FIG. 7

Regression analysis of Tomo_H
(Model summary)
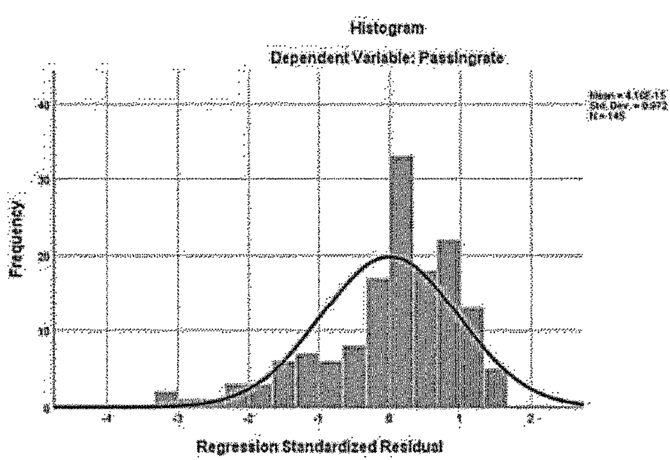
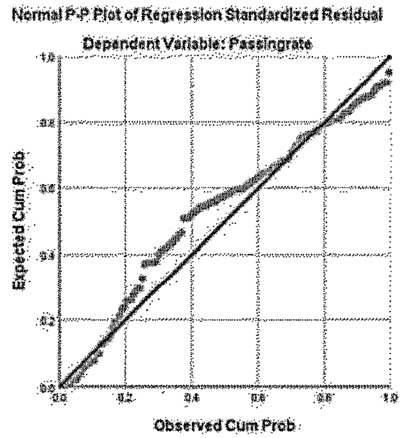
FIG. 8

Regression analysis of Tomo_H
(Regression analysis of plan parameter)

| | B | Std. Error | Beta | t | Sig. | Tolerance | VIF |
|---|---|---|---|---|---|---|---|
| (Constant) | 99.325 | 1.853 | | 53.590 | 0.000 | | |
| Dose per Fx | .246 | .236 | .080 | 1.042 | .299 | .937 | 1.067 |
| IEC Xf | .018 | .012 | .121 | 1.533 | .128 | .888 | 1.126 |
| IEC Yf | -.056 | .025 | -.177 | -2.261 | .025** | .910 | 1.099 |
| IEC Yf | -.007 | .004 | -.128 | -1.653 | .101 | .925 | 1.081 |
| Field Width | .047 | .036 | .108 | 1.294 | .198 | .795 | 1.258 |
| Modulation Factor | -.459 | .150 | -.231 | -3.069 | .003*** | .976 | 1.025 |
| Pitch | .855 | 4.537 | .015 | .189 | .851 | .854 | 1.172 |
| Control Point # | -.001 | .000 | -.245 | -2.816 | .006*** | .735 | 1.361 |

$P^{*}<0.1$ $p^{}<0.05$ $p^{*}<0.01$

Regression equation : $Y = 99.325 - 0.056X_{IEC\,Yf} - 0.459X_{MF} - 0.001X_{CP}$

FIG. 9

Regression analysis of Tomo_R
(Model summary)

*[Model Summary]*

| | R | R Square | Adjusted R Square | Std. Error of the Estimate | Durbin-Watson |
|---|---|---|---|---|---|
| **Model** | 0.494 | 0.244 | 0.144 | Model | 2.567 |

*[ANOVA]*

| | Sum of squares | df | Mean Square | F | Sig. |
|---|---|---|---|---|---|
| **Regression** | 1.704 | 8 | 0.213 | 2.456 | 0.022 |
| **Residual** | 5.290 | 81 | 0.087 | | |
| **Total** | 6.994 | 89 | | | |

**df : Degree of freedom*

FIG. 10

Regression analysis of Tomo_R
(Model summary)
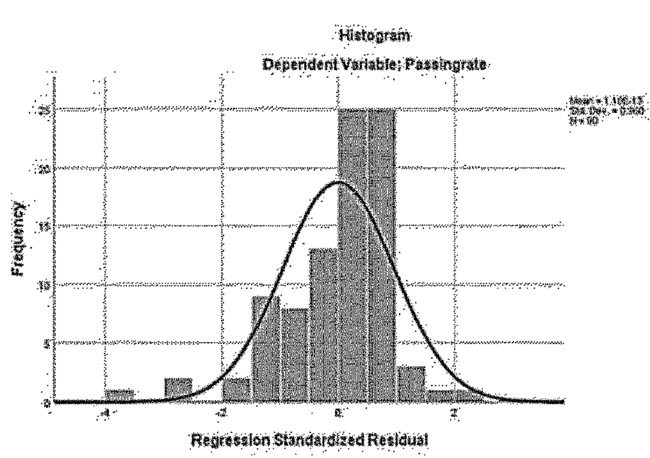
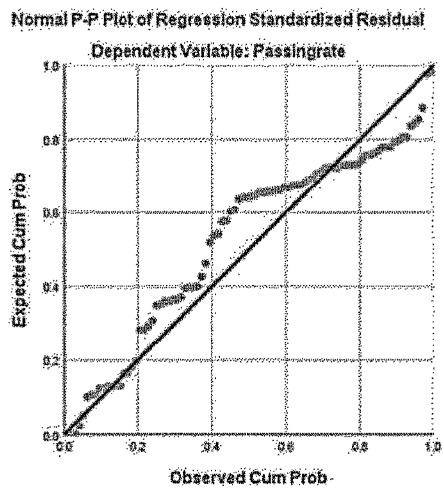
FIG. 11

Regression analysis of Tomo_R
(Regression analysis of plan parameter)

| | B | Std. Error | Beta | t | Sig. | Tolerance | VIF |
|---|---|---|---|---|---|---|---|
| (Constant) | 99.790 | 0.574 | | 173.783 | 0.000 | | |
| Dose per Fx | .016 | .028 | .069 | .551 | .584 | .788 | 1.270 |
| IEC Xf | -.010 | .003 | -.457 | -3.948 | .000*** | .924 | 1.082 |
| IEC Yf | -8.554E-5 | .000 | -.021 | -.187 | .853 | .962 | 1.039 |
| IEC Yf | .001 | .002 | .060 | .505 | .616 | .890 | 1.124 |
| Field Width | -.002 | .004 | -.075 | -.619 | .538 | .841 | 1.188 |
| Modulation Factor | .047 | .085 | .068 | .554 | .582 | .822 | 1.217 |
| Pitch | -.482 | .473 | -.125 | -1.020 | .312 | .827 | 1.209 |
| # Control Points | -6.497E-5 | .000 | -.125 | -1.022 | .311 | .832 | 1.202 |

Regression equation : $Y = 99.790 - 0.010X_{IEC\ Xf}$

FIG. 12

METHOD AND APPARATUS FOR CARRYING OUT DOSE DELIVERY QUALITY ASSURANCE FOR HIGH-PRECISION RADIATION TREATMENT

TECHNICAL FIELD

The present disclosure relates to a method for carrying out dose delivery quality assurance (DQA) for high-precision radiation treatment, and more particularly to, a method for carrying out dose DQA for high-precision radiation treatment, which is improved to establish a prediction model with respect to parameters for establishing a treatment plan of a subject to be treated and a pass rate of DQA when Tomotherapy radiation treatment is performed, and to enhance the efficiency of dose DQA and a treatment efficiency through the prediction model.

BACKGROUND ART

In a high-precision radiation treatment such as IMRT, including Tomotherapy, as shown in FIG. 1, in order to evaluate the accuracy of patient-specific treatment plans and beam irradiation, dose delivery quality assurance (DQA) is currently performed as a patient-specific quality assurance. This DQA is one of very important processes that can directly affect a patient treatment.

As shown in FIG. 2, the DQA is performed after radiation treatment planning, and a result is obtained by performing gamma analysis using a known commercialization program. At this time, the result is analyzed as a pass rate % by using a dose difference % diff per gamma analysis distance mm, and the pass rate is basically determined with respect to 3%/3 mm. When the pass rate does not exceed a certain pass rate, a DQA re-measurement is performed, and when the pass rate does not exceed the pass rate during the re-measurement, a re-treatment plan is performed.

The DQA pass rate can vary depending on radiation treatment planning parameters (hereinafter referred to as plan parameters), and has a direct effect on a patient treatment. Therefore, a research as to which plan parameter changes a DQA result is required.

PRIOR ART DOCUMENTS (Patent Document 1) Korean Patent Publication No. 10-1937651

(Patent Document 2) Korean Patent Publication No. 10-1435497

DISCLOSURE

Technical Problem

The present disclosure is designed to solve the problems of the related art, and therefore the present disclosure is directed to providing a method for carrying out dose delivery quality assurance (DQA) for high-precision radiation treatment, in which a correlation between parameters for establishing a patient's treatment plan and a pass rate of the dose DQA is derived when Tomotherapy radiation treatment is performed, and parameters and the pass rate of the dose DQA can be predicted from the derived correlation before actual dose DQA is performed, such that the efficiency of dose DQA and the treatment efficiency can be enhanced.

Technical Solution

In one aspect of the present disclosure, there is provided a method for carrying out dose delivery quality assurance (DQA) for high-precision radiation treatment including a correlation deriving step of establishing, by a data analysis unit, a parameter affecting a pass rate and a prediction model for the pass rate by deriving a correlation between parameter data of a subject to be treated who has completed high-precision radiation treatment including Tomotherapy and the pass rate of dose DQA based on regression analysis, a parameter selection step of extracting, by a parameter selection unit, parameters affecting the pass rate of dose DQA derived from the correlation deriving step from among parameters for establishing a treatment plan of a subject to be radiation treated, a pass rate calculation step of receiving, by a control unit, a variable value of the subject to be treated corresponding to the parameters extracted in the parameter selection step, and calculating, by a calculation unit, a predicted value of the pass rate of dose DQA by substituting the variable value into an equation related to the pass rate prediction model based on a control command of the control unit, and a pass rate determination step of determining, by a determination unit, firstly determining whether the predicted value of the pass rate calculated in the pass rate calculation step meets a preset prediction threshold, when the predicted value of the pass rate meets the prediction threshold as a result of determination, carrying out dose DQA according to the treatment plan, and secondly determining whether the predicted value of the pass rate meets a preset execution threshold as a result of carrying out dose DQA, wherein actual treatment is performed only when both of the first and second determination results meet the threshold.

The parameters extracted in the parameter selection step may include a Y coordinate value of a Tomotherapy radiation irradiation equipment according to a position of the subject to be treated, a maximum leaf opening time of a multi-leaf collimator (MLC), which is one of components of the Tomotherapy radiation irradiation equipment, and a number of control points corresponding to radiation projection points arranged at intervals in a circumferential direction of 360 degrees.

An equation with respect to the prediction model may be $Y=99.325-0.056*X_1-0.459*X_2-0.001*X_3$ (where, Y is a predicted value of the pass rate, $X_1$ is the Y coordinate value of the Tomotherapy radiation irradiation equipment according to the position of the subject to be treated, $X_2$ is the maximum leaf opening time, and $X_3$ is the number of control points).

An equation with respect to the prediction model may be $Y=99.790-0.010*X_4$ (where, $X_4$ is an X coordinate value of the Tomotherapy radiation irradiation equipment according to the position of the subject to be treated).

In another aspect of the present disclosure, there is provided an apparatus for carrying out dose delivery quality assurance (DQA) for high-precision radiation treatment including a data analysis unit configured to establish a parameter affecting a pass rate and a prediction model for the pass rate by deriving a correlation between parameter data of a subject to be treated who has completed high-precision radiation treatment including Tomotherapy and the pass rate of dose DQA based on regression analysis, a parameter selection unit configured to extract parameters affecting the pass rate of dose DQA derived by the data analysis unit from among parameters for establishing a treatment plan of the subject to be radiation treated, a calculation unit configured to calculate a predicted value of the pass rate of dose DQA by substituting a variable value (a variable value of the subject to be treated corresponding to the parameters extracted in the parameter selection step) received from a data input unit into an equation related to the pass rate prediction model based on a control command of the control unit, and a determination unit configured to firstly determine whether the predicted value of the pass rate calculated by the calculation unit meets a preset prediction threshold, when the predicted value of the pass rate meets the prediction threshold as a result of determination, carry out dose DQA according to the treatment plan, and secondly determine whether the predicted value of the pass rate meets a preset execution threshold as a result of carrying out the dose DQA, wherein actual treatment is performed only when both of the first and second determination results meet the threshold.

Advantageous Effects

According to the present disclosure having the configuration described above, the method for carrying out dose DQA for high-precision radiation treatment, in which parameters affecting a pass rate of dose DQA can be derived through regression analysis, which is a known statistical analysis method, and a pass rate prediction model capable of predicting each parameter and the pass rate of dose DQA can be derived, and accordingly, it can be predicted in advance whether dose DQA will be passed according to the parameters through the above prediction model, without repeatedly carrying out dose DQA according to a patient's treatment plan, and as a result, the efficiency of dose DQA can be enhanced, and the time or capacity required for such quality assurance is reduced, such that radiation treatment for an actual patient can be quickly and precisely carried out.

DESCRIPTION OF DRAWINGS

FIG. 6 is diagrams for explaining regression analysis factors used in the present embodiment.

FIG. 7 is a diagram showing a regression analysis result for Tomotherapy hi-art (Tomo_H) among two models related to a Tomotherapy device used for implementation of the present embodiment.

FIG. 8 is a diagram of a histogram and a P-P graph of a regression model related to Tomotherapy hi-art among the two models related to the Tomotherapy device.

FIG. 9 is a table of a regression analysis result of a Tomotherapy hi-art device carried out to implement a correlation deriving step which is a part of the present embodiment.

FIG. 10 is a diagram showing a regression analysis result for Radixact X9 (Tomo_R) among the two models of the Tomotherapy device.

FIG. 11 is a diagram of a histogram and a P-P graph of a regression model related to Radixact X9 (Tomo_R) among the two models related to the Tomotherapy device.

FIG. 12 is a table of regression analysis result of a Radixact X9 (Tomo_R) device carried out to implement the correlation deriving step which is a part of the present embodiment.

MODE FOR DISCLOSURE

Figure 1:
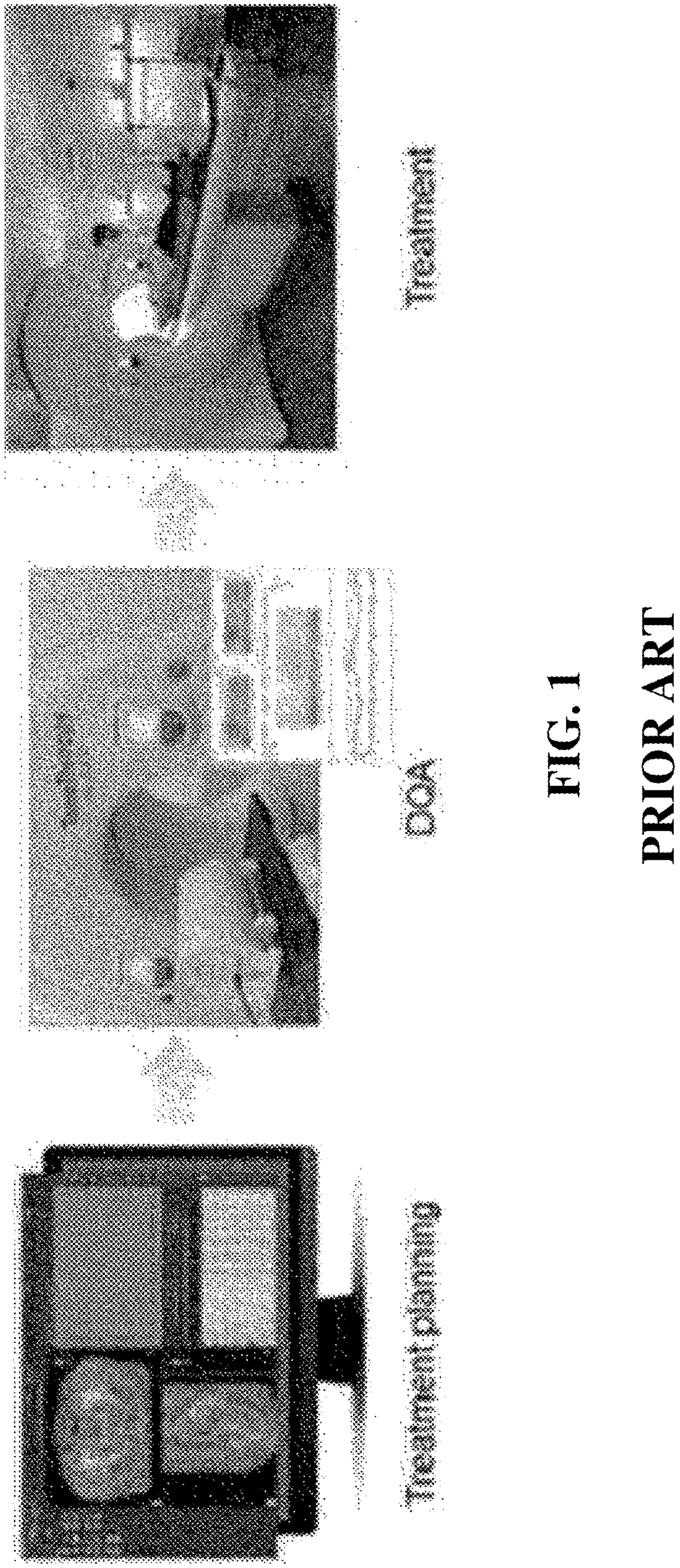
FIGS. 1 and 2 are diagrams for explaining a high-precision radiation treatment process such as IMRT including Tomotherapy according to the related art.
Figure 2:
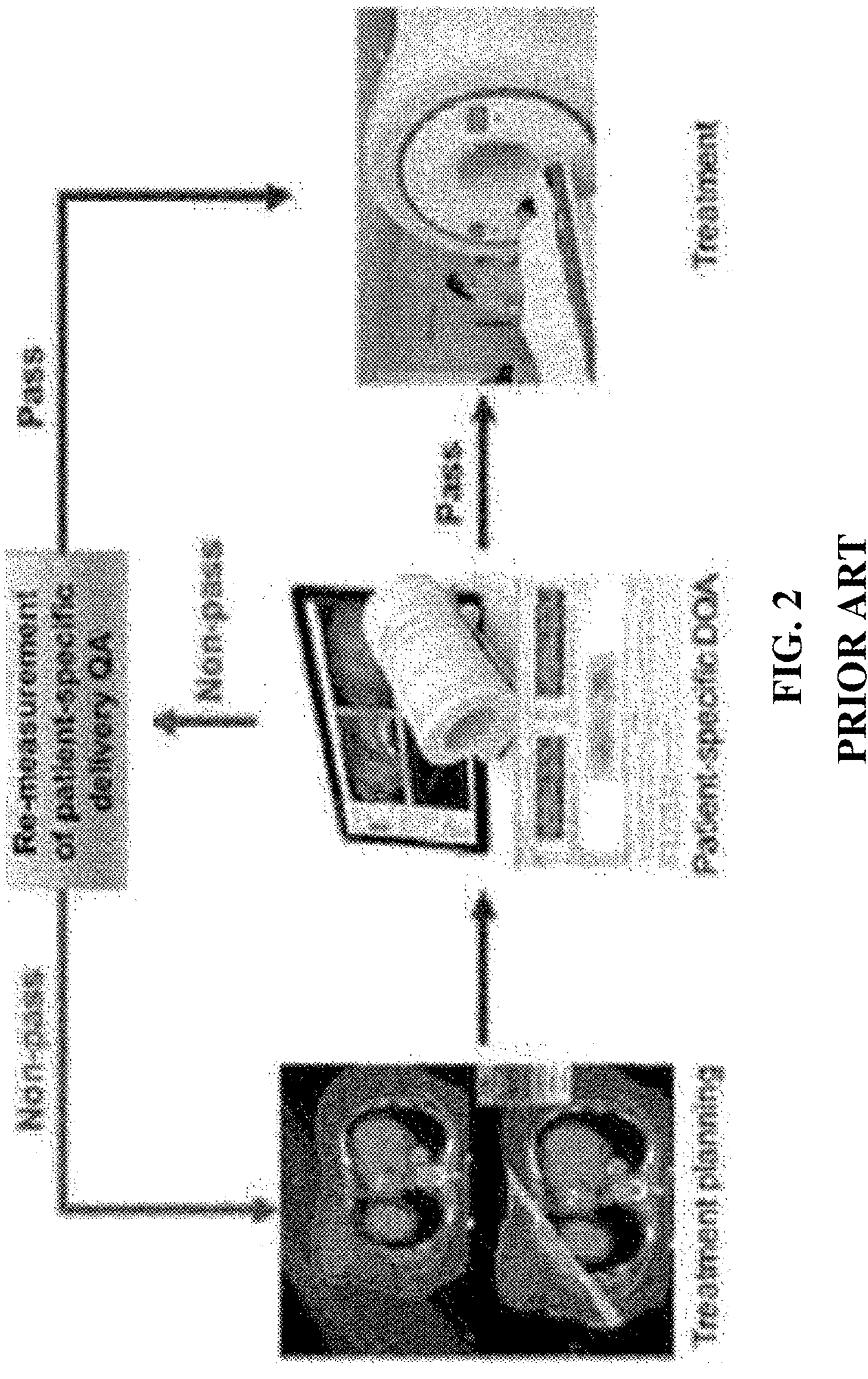

In order to clarify the understanding of the present disclosure in the following description, descriptions of known techniques for the features of the present disclosure will be omitted. The following embodiment is a detailed description to aid understanding of the present disclosure, and it will be obvious that the following embodiment does not limit the scope of the present disclosure. Therefore, an equivalent invention that performs the same function as the present disclosure will also fall within the scope of the present disclosure.

And, in the following description, the same reference numeral means the same configuration, and an unnecessary redundant description and a description of known technology will be omitted. In addition, the following description of each embodiment of the present disclosure redundant with the description of the background art of the present disclosure will also be omitted.

Hereinafter, a method for carrying out dose delivery quality assurance (DQA) for high-precision radiation treatment according to an embodiment of the present disclosure will be described in detail.

Figure 3:
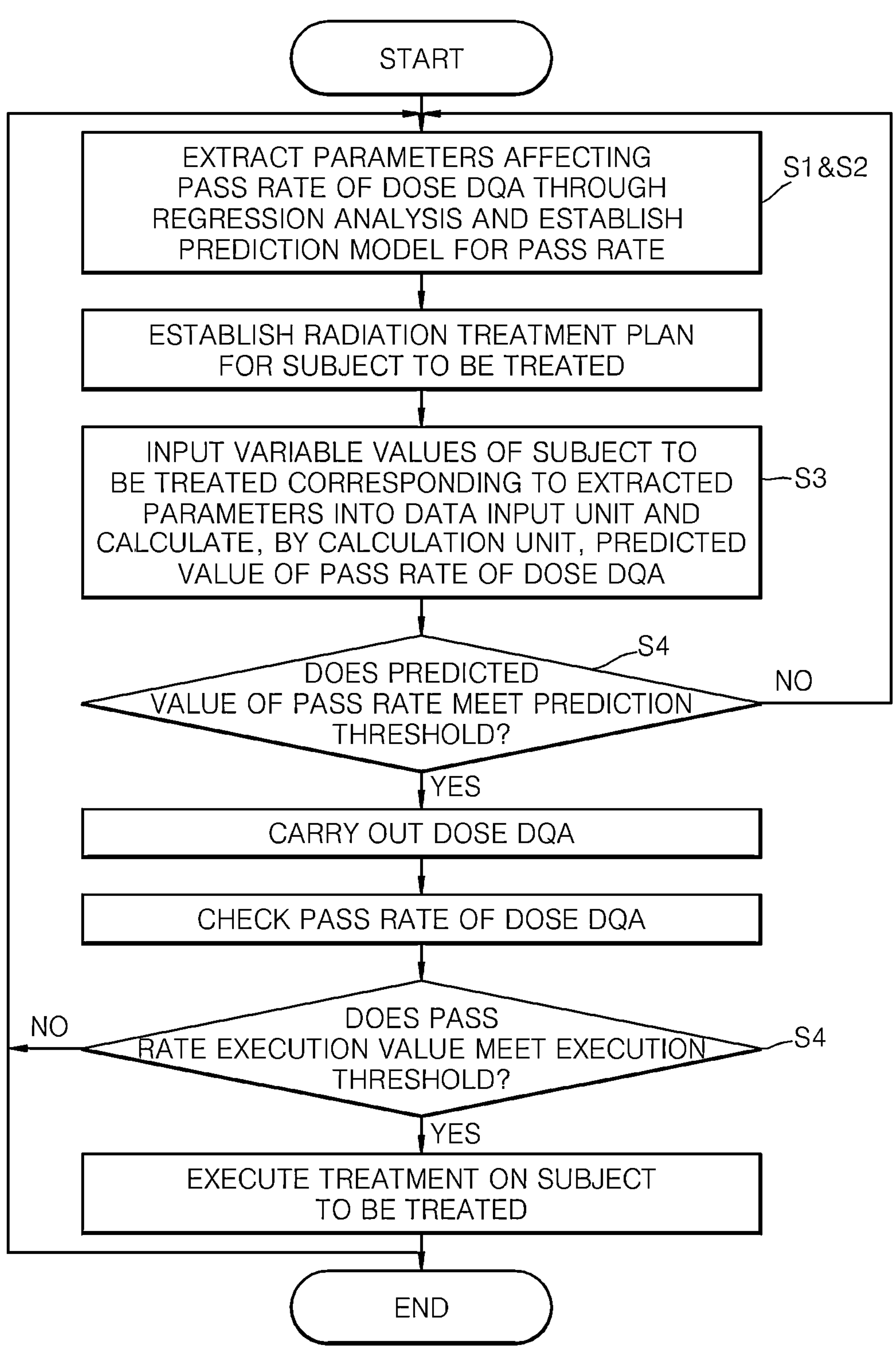
FIG. 3 is a flowchart for explaining the logic flow of a method for carrying out dose delivery quality assurance (DQA) for high-precision radiation treatment according to an embodiment of the present disclosure.
Figure 4:
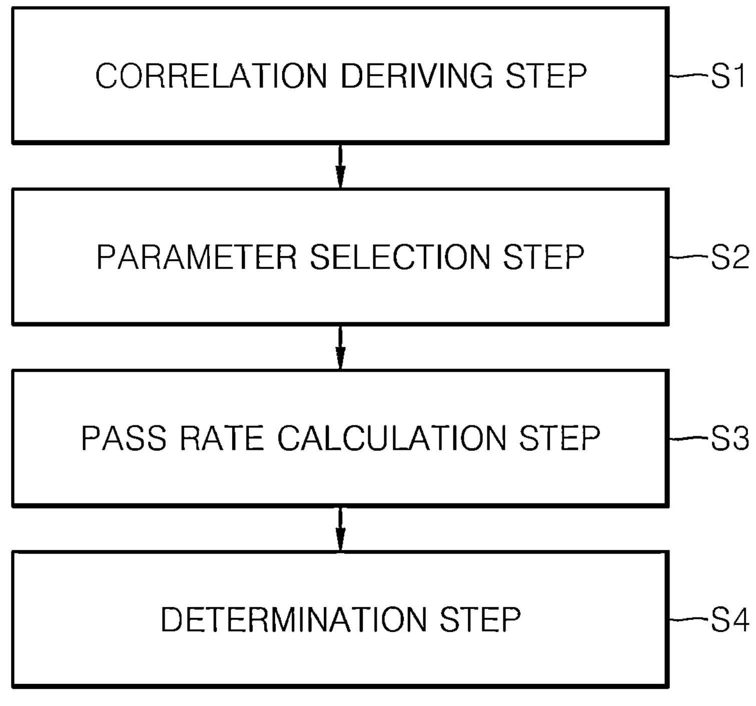
FIG. 4 is a block diagram showing a configuration according to an embodiment of the present disclosure according to a process sequence.
Figure 5:
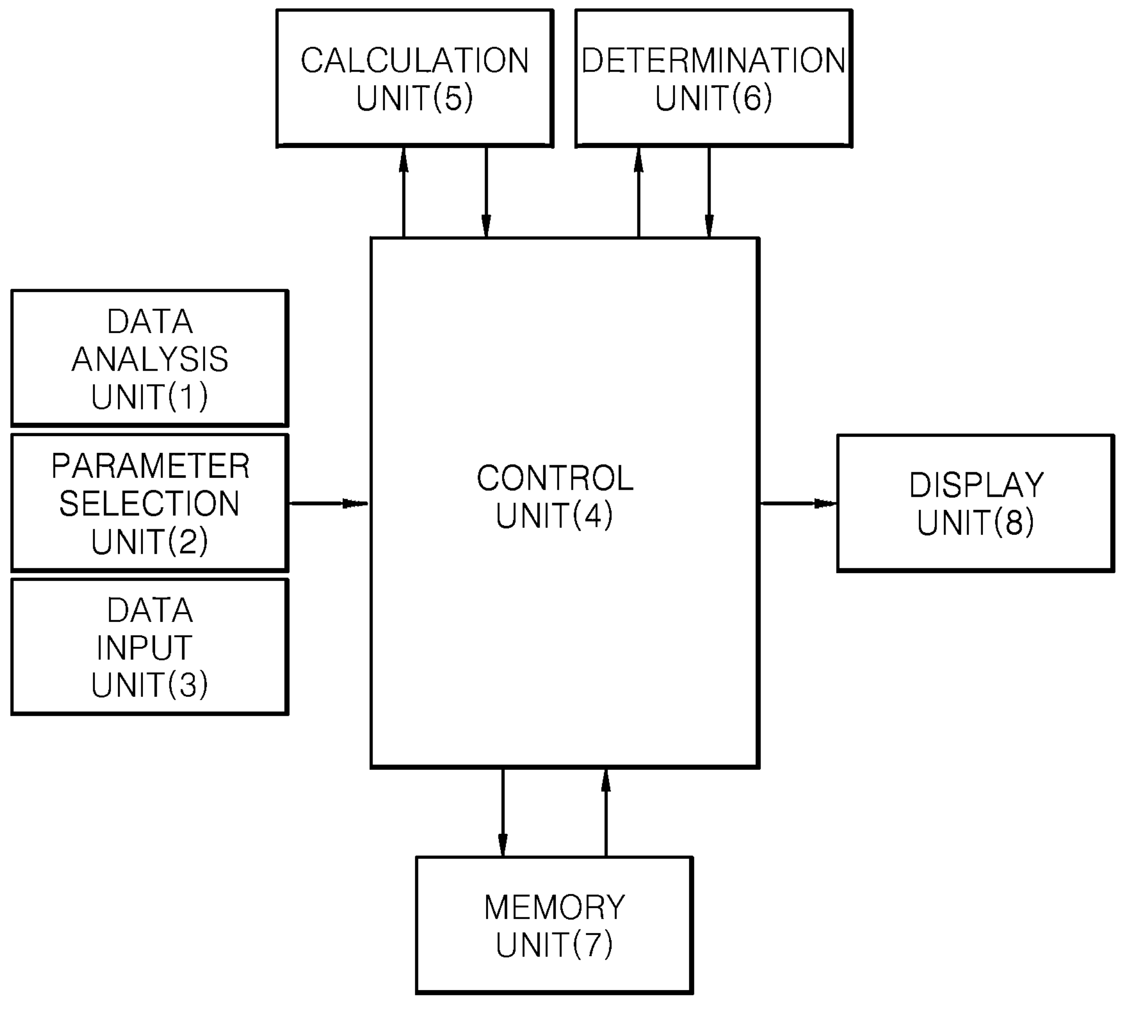
FIG. 5 is a block diagram showing a device configuration for implementing an embodiment of the present disclosure.

FIG. 3 is a flowchart for explaining the logic flow of a method for carrying out dose DQA for high-precision radiation treatment according to an embodiment of the present disclosure. FIG. 4 is a block diagram showing a configuration according to an embodiment of the present disclosure according to a process sequence. FIG. 5 is a block diagram showing a device configuration for implementing an embodiment of the present disclosure. FIG. 6 is diagrams for explaining regression analysis factors used in the present embodiment. FIG. 7 is a diagram showing a regression analysis result for Tomotherapy hi-art (Tomo_H) among two models related to a Tomotherapy device used for implementation of the present embodiment. FIG. 8 is a diagram of a histogram and a P-P graph of a regression model related to Tomotherapy hi-art among the two models related to the Tomotherapy device. FIG. 9 is a table of a regression analysis result of a Tomotherapy hi-art device carried out to implement a correlation deriving step which is a part of the present embodiment.

As shown in FIGS. 3 to 5, the method for carrying out dose DQA for high-precision radiation treatment according to an embodiment of the present disclosure includes a correlation deriving step (S1), a parameter selection step (S2), a pass rate calculation step (S3), and a determination step (S4).

In the correlation deriving step (S1) relating to a step performed by a data analysis unit 1, a process of establishing a parameter affecting a pass rate and a prediction model for the pass rate by deriving a correlation between parameter data of a subject to be treated who has completed high-precision radiation treatment including Tomotherapy and a pass rate of dose DQA based on regression analysis is performed.

Here, the parameter means a planning target volume (PTV) of the subject to be treated, a dose per fraction, a size of dose required for radiation treatment using Tomotherapy, X, Y, and Z coordinate values of radiation irradiation equipment, the maximum leaf opening time of a multi-leaf collimator (MLC), a control point called a projection in Tomotherapy, etc.

In addition, regression analysis is an analysis method that statistically estimates the relationship between variables by using a parametric model, and is widely known to be used to mainly determine the effect of an independent variable on a dependent variable.

Regression analysis factors used in the present embodiment are described with reference to FIG. 6 as follows.

That is, a SPSS 25 (manufacturer; IBM, model name; SPSS Statistics 25) version was used as a tool for regression analysis, and $R^2$ means 1—(MSE of a regression line of mean square error of a data mean), which shows how much a derived regression line matches a variance of data. Durbin Watson (DW) is between 1 and 3, and may make it possible to determine that there is no autocorrelation, that is, correlation, between residuals, and ANOVA is an abbreviation of analysis of variance, and may make it possible to know whether a derived regression equation is appropriate when a P-value is 0.05 or less.

VIF is an abbreviation of variance inflation factor. When VIF is less than 10, it means that there is no problem with multicollinearity (a phenomenon in which some prediction variables in regression analysis have a high degree of correlation with other prediction variables, which has a negative effect). Beta means the influence of an independent variable on a dependent variable, and the closer to 1, the stronger the influence. A t value is a coefficient divided by a standard error, and may make it possible to determine the appropriateness of the regression equation together with the p-value.

In the present embodiment, because the configuration and performance of the Tomotherapy machine on which regression analysis was performed are different for each version, regression analysis was performed for each version.

That is, regression analysis was performed on Tomotherapy hi-art, which is a relatively initial model among Tomotherapy machines, and Radixact X9 machine, which is the latest model.

As a result of regression analysis on Tomotherapy hi-art (Tomo_H) among the above two models, as shown in FIG. 7, it can be seen from the model summary that because R square and adjusted R square are 0.246 and 0.201, respectively, and Durbin Watson is 1.774 between 1 and 3, there is no autocorrelation, and that a regression model derived with a p-value of 0.000 is appropriate as a result of ANOVA. Also, FIG. 8 is the diagram of the histogram and the P-P graph of the regression model related to Tomotherapy hi-art, which suggests that regression standardized residuals satisfy normality.

FIG. 9 is the table of the regression analysis result of the Tomotherapy hi-art device carried out to implement the correlation deriving step which is a part of the present embodiment. As shown in this figure, as a result of regression analysis, three statistically significant parameters were derived as IEC Y coordinate, modulation factor, and the number of control point, and it can be seen that because the t value of each parameter is negative, a passing rate decreases as values of the corresponding parameters increase.

Here, the IEC Y coordinate is a Y coordinate value of a Tomotherapy radiation irradiation equipment according to a position of the subject to be treated, the modulation factor means the maximum leaf opening time of a multi-leaf collimator (MLC), which is one of components of the Tomotherapy radiation irradiation equipment, and the number of control points corresponds to radiation projection points arranged at intervals in a circumferential direction of 360 degrees.

As described above, in the present embodiment, parameters affecting a pass rate of dose delivery quality assurance can be derived through regression analysis, which is a known statistical analysis method, and a pass rate prediction model capable of predicting each parameter and the pass rate of dose delivery quality assurance can be derived, and accordingly, it can be predicted in advance whether dose delivery quality assurance will be passed according to the parameters through the above prediction model, without repeatedly carrying out dose DQA according to a patient's treatment plan, and as a result, advantages in that the efficiency of dose delivery quality assurance can be enhanced, and the time or capacity required for such quality assurance is reduced, such that radiation treatment for an actual patient can be quickly and precisely carried out can be expected.

An equation with respect to the prediction model derived in the correlation deriving step (S1) is $Y=99.325-0.056*X_1-0.459*X_2-0.001*X_3$ (where, Y is a predicted value of the pass rate, $X_1$ is the Y coordinate value of the Tomotherapy radiation irradiation equipment according to the position of the subject to be treated, $X_2$ is the maximum leaf opening time, and $X_3$ is the number of control points.)

In the parameter selection step (S2) employed in the present embodiment relating to a step performed by a parameter selection unit 2, a process of extracting parameters affecting the pass rate of dose DQA derived from the correlation deriving step from among parameters for establishing a treatment plan of a subject to be radiation treated is performed.

That is, the parameters extracted in the parameter selection step are the Y coordinate value of the Tomotherapy radiation irradiation equipment according to the position of the subject to be treated, the maximum leaf opening time of the MLC, which is one of components of the Tomotherapy radiation irradiation equipment, and the number of control points corresponding to the radiation projection points arranged at intervals in the circumferential direction of 360 degrees described above.

In the pass rate calculation step (S3) employed in the present embodiment, a calculation unit 5 performs a process of calculating a predicted value of the pass rate value of dose DQA by substituting a variable value (a variable value of the subject to be treated corresponding to the parameter extracted by a control unit 4 in the parameter selection step) into the equation related to the pass rate prediction model based on a control command of the control unit 4.

The present embodiment can fundamentally block unnecessary and repetitive dose DQA through such a prediction of the dose DQA pass rate, thereby increasing the efficiency of quality assurance.

Also, in the determination step (S4) employed in the present embodiment relating to a step performed by a determination unit 6, it is firstly determined whether the predicted value of the pass rate calculated in the pass rate calculation step (S3) meets a preset prediction threshold, when the predicted value of the pass rate meets the prediction threshold as a result of determination, dose DQA is carried out according to the treatment plan, and it is secondly determined whether the predicted value of the pass rate meets a preset execution threshold as a result of carrying out dose DQA, and thus, actual treatment can be performed only when both the first and second determination results meet the threshold.

In the present embodiment having such a configuration, the efficiency of quality assurance can be increased by carrying out the dose DQA only when the predicted value of the pass rate according to the parameter meets the preset prediction threshold, and furthermore, actual treatment can be finally performed only when the predicted value of the pass rate meets an actual execution threshold as a result of carrying out the dose DQA, such that the precision and safety of treatment can be enhanced.

On the other hand, as shown in FIG. 5, the apparatus for carrying out dose DQA for high-precision radiation treatment according to an embodiment of the present disclosure includes the data analysis unit 1, the parameter selection unit 2, the control unit 4, the calculation unit 5, and the determination unit 6.

The data analysis unit 1 establishes a parameter affecting a pass rate and a prediction model for the pass rate by deriving a correlation between parameter data of a subject to be treated who has completed high-precision radiation treatment including Tomotherapy and the pass rate of dose DQA based on regression analysis.

The parameter selection unit 2 extracts parameters affecting the pass rate of dose DQA derived by the data analysis unit 1 from among parameters for establishing a treatment plan of the subject to be radiation treated.

The calculation unit 5 calculates the predicted value of the pass rate of dose DQA by substituting a variable value (a variable value of the subject to be treated corresponding to the parameters extracted in the parameter selection step) received from a data input unit 3 into the equation related to the pass rate prediction model based on a control command of the control unit 4.

The determination unit 6 firstly determines whether the predicted value of the pass rate calculated by the calculation unit 5 meets a preset prediction threshold, when the predicted value of the pass rate meets the prediction threshold as a result of determination, carries out dose DQA according to the treatment plan, and secondly determines whether the predicted value of the pass rate meets a preset execution threshold as a result of carrying out dose DQA, and as a result, actual treatment can be performed only when both the first and second determination results meet the threshold.

The apparatus for carrying out dose DQA for high-precision radiation treatment having such a configuration according to an embodiment of the present disclosure is configured that the calculation unit 5 can predict the pass rate of dose DQA by substituting a parameter value selected by the parameter selection unit 2 into the prediction model derived by the data analysis unit 1, without repeatedly carrying out dose DQA according to a patient's treatment plan, which derives an advantage of increasing the efficiency of quality assurance by fundamentally blocking unnecessary and repetitive dose DQA through such a prediction of the dose DQA pass rate, and an advantage of quickly and precisely carrying out radiation treatment for an actual patient by reducing the time or capacity required for quality assurance.

Hereinafter, a regression analysis result for Radixact X9 (Tomo_R) among two models of a Tomotherapy device employed for the implementation of the present embodiment is described with reference to FIGS. 10 to 12.

FIG. 10 is a diagram showing the regression analysis result for Radixact X9 (Tomo_R) among the two models of the Tomotherapy device. FIG. 11 is a diagram of a histogram and a P-P graph of a regression model related to Radixact X9 (Tomo_R) among the two models related to the Tomotherapy device. FIG. 12 is a table of a regression analysis result of a Radixact X9 (Tomo_R) device carried out to implement the correlation deriving step which is a part of the present embodiment.

As a result of regression analysis for Radixact X9 (Tomo_R), as shown in FIG. 10, it can be seen from the model summary that because R square and adjusted R square are 0.244 and 0.144, respectively, and Durbin Watson is 2.567 between 1 and 3, there is no autocorrelation, and that a regression model derived with a p-value of 0.022 is appropriate as a result of ANOVA. Also, FIG. 11 is the diagram of the histogram and the P-P graph of the regression model related to Radixact X9(Tomo_R), which suggests that regression standardized residuals satisfy normality.

Also, as well shown in FIG. 12, one statistically significant parameter is IEC X coordinate, and it can be seen that because the t value is negative, a passing rate decreases as an X coordinate value increases. Here, the IEC X coordinate is an X coordinate value of a Tomotherapy radiation irradiation equipment according to a position of the subject to be treated.

An equation with respect to the prediction model derived through regression analysis related to Radixact X9 (Tomo_R) is $Y=99.790-0.010*X_4$ (where, $X_4$ is the X coordinate value of the Tomotherapy radiation irradiation equipment according to the position of the subject to be treated.)

Although various embodiments of the present disclosure have been described above, the present embodiment and the accompanying drawings only clearly show part of the technical idea included in the present disclosure, and it will be apparent that modified examples and specific embodiments that can be easily inferred by ordinary skilled in the art within the scope of the technical idea included in the specification and drawings of the present disclosure are all included in the scope of the present disclosure.

What is claimed is:

1. A method, implemented by a controller, for carrying out dose delivery quality assurance (DQA) for high-precision radiation treatment, the method comprising:

a correlation deriving step of establishing a parameter affecting a pass rate of dose DOA and a pass rate prediction model by deriving a correlation between parameter data of a subject to be treated who has completed high-precision radiation treatment comprising Tomotherapy and the pass rate of dose DQA based on regression analysis;

a parameter selection step of extracting parameters affecting the pass rate of dose DQA derived from the correlation deriving step from among parameters for establishing a treatment plan of a subject to be radiation treated, wherein the parameters extracted include a Y coordinate value of a Tomotherapy radiation irradiation equipment according to a position of the subject to be treated, a maximum leaf opening time of a multi-leaf collimator (MLC), which is a component of the Tomotherapy radiation irradiation equipment, and a number of control points corresponding to radiation projection points arranged at intervals in a circumferential direction of 360 degrees;

a pass rate calculation step of receiving a variable value of the subject to be treated corresponding to the parameters extracted in the parameter selection step, and calculating a predicted value of the pass rate of dose DQA by substituting the variable value into an equation related to the pass rate prediction model based on a control command of the controller; and a pass rate determination step of performing a first determination of whether the predicted value of the pass rate calculated in the pass rate calculation step meets a preset prediction threshold, when the predicted value of the pass rate meets the preset prediction threshold as a result of the first determination, carrying out the dose DQA according to the treatment plan, and performing a second determination of whether an execution value of the pass rate meets a preset execution threshold as a result of carrying out the dose DQA, wherein, when the predicted value of the pass rate does not meet the preset prediction threshold, repeating from the correlation derivation step to re-establish the treatment plan by modifying the variable value of the parameters until the predicted value of the pass rate meets the preset prediction threshold before the dose DOA is carried out, and wherein actual treatment is performed only when both results of the first determination and the second determination meet respective thresholds.

2. The method of claim 1, wherein an equation with respect to the pass rate prediction model is $Y=99.325-0.056*X_1-0.459*X_2-0.001*X_3$, wherein Y is a predicted value of the pass rate, $X_1$ is the Y coordinate value of the Tomotherapy radiation irradiation equipment according to the position of the subject to be treated, $X_2$ is the maximum leaf opening time, and $X_3$ is the number of control points.

3. The method of claim 1, wherein an equation with respect to the pass rate prediction model is $Y=99.790-0.010*X_4$, wherein $X_4$ is an X coordinate value of the Tomotherapy radiation irradiation equipment according to the position of the subject to be treated.

4. An apparatus for carrying out dose delivery quality assurance DQA) for high-precision radiation treatment, the apparatus comprising:

a memory;

a controller configured to:

establish a parameter affecting a pass rate of dose DOA and a pass rate prediction model by deriving a correlation between parameter data of a subject to be treated who has completed high-precision radiation treatment including Tomotherapy and the pass rate of dose DQA based on regression analysis;

extract parameters affecting the pass rate of dose DQA derived by the controller from among parameters for establishing a treatment plan of the subject to be radiation treated, wherein the parameters extracted include a Y coordinate value of a Tomotherapy radiation irradiation equipment according to a position of the subject to be treated, a maximum leaf opening time of a multi-leaf collimator (MLC), which is a component of the Tomotherapy radiation irradiation equipment, and a number of control points corresponding to radiation projection points arranged at intervals in a circumferential direction of 360 degrees;

calculate a predicted value of the pass rate of dose DQA by substituting a variable value of the subject to be treated corresponding to the extracted parameters into an equation related to the pass rate prediction model based on a control command of the controller; and perform a first determination of whether the predicted value meets a preset prediction threshold, when the predicted value of the pass rate meets the preset prediction threshold as a result of the first determination, carry out the dose DQA according to the treatment plan, and perform a second determination of whether the predicted value of the pass rate meets a preset execution threshold as a result of carrying out the dose DQA, wherein, when the predicted value of the pass rate does not meet the preset prediction threshold, re-establishing the treatment plan by modifying the variable value of the parameters until the predicted value of the pass rate meets the preset prediction threshold before the dose DOA is carried out, and wherein actual treatment is performed only when both results of the first determination and the second determination meet respective thresholds.

* * * * *